United States Patent [19]

Tabei et al.

[11] Patent Number: 5,286,891
[45] Date of Patent: Feb. 15, 1994

[54] HYDROXY-TERMINATED POLYSILANE AND PROCESS FOR MAKING

[75] Inventors: Eiichi Tabei; Shigeru Mori, both of Kawasaki, Japan

[73] Assignee: Shin-Etsu Chemical Co., Ltd., Tokyo, Japan

[21] Appl. No.: 6,482

[22] Filed: Jan. 21, 1993

[30] Foreign Application Priority Data

Jan. 21, 1992 [JP] Japan .................................. 4-030104

[51] Int. Cl.$^5$ .............................................. C07F 7/08
[52] U.S. Cl. .................................................. 556/430
[58] Field of Search ......................................... 556/430

[56] References Cited

U.S. PATENT DOCUMENTS 3,637,781  1/1972  Barquin et al. ..................... 556/430
4,952,658  8/1990  Kalchauer et al. ............. 556/430 X
5,041,588  8/1991  Caporiccio ....................... 556/430 X
5,166,287 11/1992  Kalchauer et al. ............. 556/430 X

*Primary Examiner*—Paul F. Shaver
*Attorney, Agent, or Firm*—Birch, Stewart, Kolasch & Birch

[57] ABSTRACT

The invention provides a novel hydroxy terminated polysilane of the formula:

$$OH[(R^1R^2Si)_n(R^3R^4Si)_m]_kOH$$

wherein $R^1$, $R^2$, $R^3$ and $R^4$ are alkyl or aryl groups, n, m and k are numbers in the range: $0 \leq n \leq 10$, $0 \leq m \leq 10$, $n+m \geq 10$, and $k \geq 1$, especially $k \geq 5$. It is prepared by hydrolyzing a chloro- terminated polysilane.

15 Claims, No Drawings

HYDROXY-TERMINATED POLYSILANE AND PROCESS FOR MAKING

BACKGROUND OF THE INVENTION

1. Field of the Invention

This invention relates to $\alpha, \omega$-hydroxy terminated polysilane capable of accepting any desired functional group and useful as a source material for forming copolymers with other polymers as well as a process for preparing the same.

2. Prior Art

Most industrial processes for preparing polysilanes utilize coupling reaction of dihalogenosilanes with alkali metals as reported in Journal of Polymer Science: Polymer Chemistry Edition, Vol. 22, 159-170 (1984) and Journal of Organometallic Chemistry, Vol. 300, 327 (1986). These processes produce polysilanes in the form of mixtures of cyclic polymers and halo- or hydrogen-terminated polymers. It is difficult to quantitatively obtain terminally modified polymers from these mixtures.

With respect to the synthesis of single and modified polysilanes, Sakurai et al. attempted living polymerization from polymers containing a disilane unit for introducing hydrogen or carboxylic acid as well as copolymerization of such polymers with polymethyl methacrylate (PMMA) as reported in Kagaku to Kogyo (Chemistry & Industry), Vol. 42, No. 4, 744. This attempt, however, has several industrial problems including limited type of substituents and limited availability of monomers.

Exemplary synthesis of both and single end reactive polysilanes is reported in Journal of Organometallic Chemistry, Vol. 2, 478-484 (1964) and Journal of Organometallic Chemistry, Vol. 23, 63-69 (1970). More specifically, chloro-terminated oligosilanes can be prepared by reacting permethyloligosilanes with acetyl chloride in the presence of aluminum chloride. Also chloro-terminated oligosilanes can be prepared by reacting phenyl-terminated oligosilanes with hydrogen chloride or chlorosilane in the presence of aluminum chloride. These chloro-terminated oligosilanes, however, have a low degree of polymerization.

SUMMARY OF THE INVENTION

Focusing on the reaction that on exposure to ultraviolet (UV) radiation, polysilanes decompose and convert to those of a lower molecular weight while yielding highly reactive silylene and silyl radicals as reported in Applied Organometallic Chemistry, Vol. 1, 7-14 (1987), the inventors have found that when high-molecular weight polysilanes are photodecomposed by selecting a chlorinated hydrocarbon as a solvent prone to chlorine withdrawal and exposing the polysilanes to UV radiation in the chlorinated hydrocarbon, silyl radicals generate and then form chloro-terminated polysilanes having a high degree of polymerization.

More specifically, coupling reaction of dichlorosilane with alkali metal yields a high-molecular weight polysilane which is a mixture of a cyclic polymer and a halo- or hydrogen-terminated polymer as previously mentioned. When such a polysilane is exposed to Uv radiation, the cyclic polymer opens its ring and converts into a chloro-terminated polysilane through photo-decomposition. At the same time, the halo- or hydrogen-terminated polymer remains unreactive where it has a terminal halogen atom, but where it has a terminal hydrogen atom, the hydrogen atom is replaced by a chlorine atom under the action of light or heat. As a result, from high-molecular weight polysilane, there is obtained a chloro-terminated polysilane having a lower molecular weight which is dictated by the dose of UV radiation. This chloro-terminated polysilane is the subject matter of the first one of our copending applications referred to above.

Then an object of the present invention is to convert the chloro-terminated polysilane to a hydroxy-terminated polysilane. Another object is to provide a novel and improved hydroxy-terminated polysilane with a high degree of polymerization capable of accepting any desired functional group and suitable as a source material for forming copolymers with other polymers. A further object is to provide a process for preparing such a hydroxy-terminated polysilane.

Making investigations on the synthesis of other polysilanes from the chloro-terminated polysilane, we have found that by dissolving the chloro-terminated polysilane in a polysilane-miscible solvent, and adding water to the solution for hydrolysis to take place, there is formed a hydroxy-terminated polysilane having a high degree of polymerization, which has never been reported on synthesis in the literature.

Accordingly, the present invention provides a both end hydroxy-terminated polysilane of the formula:

    (1)

wherein $R^1$, $R^2$, $R^3$ and $R^4$ are independently monovalent hydrocarbon groups having 1 to 12 carbon atoms selected from substituted or unsubstituted alkyl and aryl groups, letters n, m and k are numbers in the range: $0 \leq n \leq 10$, $0 \leq m \leq 10$, $n+m \geq 10$, and $k \geq 1$.

In a second aspect, the present invention provides a process for preparing a hydroxy-terminated polysilane by hydrolyzing a chloro-terminated polysilane.

DETAILED DESCRIPTION OF THE INVENTION

The hydroxy-terminated polysilane of the present invention is represented by formula (1).

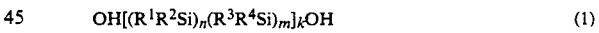    (1)

In formula (1), $R^1$, $R^2$, $R^3$ and $R^4$ which may be identical or different, are monovalent hydrocarbon groups having 1 to 12 carbon atoms, preferably 1 to 10 carbon atoms selected from substituted or unsubstituted alkyl and aryl groups. The alkyl groups include methyl, ethyl and propyl groups and the aryl groups include phenyl and tolyl groups. Letters n, m and k are numbers in the range: $0 \leq n \leq 10$, $0 \leq m \leq 10$, $n+m \geq 10$, and $k \geq 1$, preferably $k \geq 5$, more preferably $k \geq 10$. The term hydroxy-terminated means that the polysilane is terminated with hydroxyl at both ends of its molecular chain unless otherwise stated.

The hydroxy-terminated polysilane of formula (1) is prepared first by synthesizing a chloro-terminated polysilane of formula (2):

    (2)

wherein $R^1$, $R^2$, $R^3$, $R^4$, n, m and k are as defied above.

The chloro-terminated polysilane of formula (2) is prepared by effecting coupling reaction of a dichlorosilane with an alkali metal such as sodium for forming a polysilane. The dichlorosilane used herein should preclude the use of dimethyldichlorosilane alone. Aromatic group-containing dichlorosilanes such as methylphenyldichlorosilane and ethylphenyl-dichlorosilane, dichlorosilanes having a $C_2$ or higher aliphatic group such as methylethyl-dichlorosilane, methylpropyldichlorosilane, methylhexyldichlorosilane and dihexyldichlorosilane may be used alone or in admixture of two or more.

The coupling reaction results in a polysilane of the general formula (3):

wherein $R^1$, $R^2$, $R^3$ and $R^4$ are as defined above, $0 \leq n'$, $0 \leq m'$, $10 \leq n' + m'$, preferably $30 \leq n' + m'$. It preferably has a number average molecular weight (Mn) of 1,000 to 1,000,000, more preferably 5,000 to 1,000,000.

Next, the polysilane is dissolved in a chlorinated hydrocarbon solvent and exposed to UV radiation in an inert gas atmosphere. Examples of the chlorinated hydrocarbon used herein include dichloromethane, chloroform, carbon tetrachloride, 1,2-dichloroethane, 1,1,2-trichloroethane, and 1,1,2,2-tetrachloroethane alone or in admixture of two or more.

Preferably, the polysilane is dissolved in a chlorinated hydrocarbon to form a solution at a concentration of about 1 to 20% by weight, more preferably about 1 to 10% by weight. The polysilane solution is sealingly filled in a Pyrex ® or quartz reaction tube and irradiated with UV radiation in an inert gas atmosphere using a high pressure mercury lamp (312 nm), for example. The inert gas may be nitrogen or argon gas though not limited thereto. The dose of UV radiation may be properly determined since the resulting chloro-terminated polysilane has a molecular weight which depends on the UV dose.

After exposure to a predetermined dose of UV, the reaction solution is concentrated to ½ to 1/5 in volume. Hexane is added to the concentrate such that about 150 grams of hexane is available per 10 grams of the polysilane, thereby causing the chloro-terminated polysilane (Mn ≧ 1,000) to precipitate. Through filtration and drying, the end chloro-terminated polysilane is obtained as white powder.

From the chloro-terminated polysilane, a hydroxy-terminated polysilane is synthesized. Preferably the chloro-terminated polysilane is first dissolved in a polysilane-miscible solvent. Examples of the chloro-terminated polysilane which can be used herein include chloro-terminated aliphatically substituted polysilanes and chloro-terminated aromatically substituted polysilanes, such as chloro-terminated methylhexylpolysilane and chloro-terminated methylphenylpolysilane. The polysilane-miscible solvents which can be used herein include tetrahydrofuran (THF), toluene and xylene. Both the polysilanes and solvents may be used alone or in admixture of two or more. The solution preferably has a concentration of about 1 to 20% by weight, more preferably about 1 to 10% by weight.

Then a hydrolysis promoter, for example, amines such as triethylamine and pyridine may be added to the solution, preferably in an amount of 2 mol or more per mol of the chloro-terminated polysilane.

Then water is added to the solution followed by agitation. Preferably water is added in an amount of 2 mol or more per mol of the chloro-terminated polysilane. The reaction temperature is preferably from 40° C. to the reflux temperature and the reaction time is generally about 2 to 6 hours.

After the completion of reaction, the reaction solution was combined with an organic solvent such as toluene and washed with water. The organic layer is dried over a desiccant such as calcium chloride. With the desiccant filtered off, the organic layer is concentrated, obtaining a hydroxy-terminated polysilane of formula (1) as white powder.

The thus obtained hydroxy-terminated polysilane according to the present invention has hydroxyl groups at both ends thereof and thus highly reactive at the both ends, and therefore, any functional groups can be introduced at the both ends. The hydroxy-terminated polysilane may be copolymerized with other polymers to form copolymers such as dialkylhydroxy-terminated polysilanes and dialkylvinylsiloxy-terminated polysilanes. In this regard, the hydroxy-terminated polysilane is a useful source material for forming copolymers with other polymers.

EXAMPLE

Examples of the present invention are given below by way of illustration and not by way of limitation. All percents are by weight. Mn and Mw are number and weight average molecular weights, respectively, and Ph is phenyl.

First, preparation of chloro-terminated polysilanes is described.

REFERENCE EXAMPLES 1-5

Methylphenylpolysilane having Mn=24,000 and Mw/Mn=3.32 was previously prepared by coupling reaction of methylphenyldichlorosilane with sodium. 7.0 grams of methylphenylpolysilane was dissolved in 133 grams of carbon tetrachloride at a concentration of 5%. In a nitrogen gas atmosphere, a Pyrex reaction tube with a diameter of 15 Mm was filled with the polysilane solution, closed with a plug, and exposed to UV radiation (312 nm) in a dose of 1 $J/cm^2$ using a high-pressure mercury lamp. The reaction solution was concentrated to about 50 grams. Addition of 100 grams of hexane to the solution caused precipitation of a chloro-terminated polysilane of the following formula (4). It was isolated by filtration and dried, obtaining a white powder (Reference Example 1).

The procedure of Reference Example 1 was repeated except that the UV dose was changed to 2, 3, 5 and 10 $J/cm^2$, yielding white powders (Reference Examples 2-5).

Table 1 reports the Mn, Mw/Mn and yields of these white powders. Their chlorine contents as measured by titration are also reported together with the theoretical values.

TABLE 1

| UV dose ($J/cm^2$) | Chloro-terminated polysilane | | | | |
|---|---|---|---|---|---|
| | Mn* | Mw/Mn | Yield (%) | Cl (%) Found | Cl (%) Calc. |
| 1 | 15,970 | 2.34 | 77 | 0.45 | 0.45 |
| 2 | 12,220 | 1.94 | 65 | 0.54 | 0.58 |
| 3 | 11,980 | 1.93 | 63 | 0.58 | 0.59 |
| 5 | 8,300 | 1.70 | 60 | 0.84 | 0.86 |
| 10 | 4,600 | 1.47 | 52 | 1.49 | 1.53 |

*Calculated as polystyrene

Next, synthesis of a hydroxy-terminated polysilane from a chloro-terminated polysilane according to the present invention is described.

EXAMPLE 1

In 100 grams of THF was dissolved 5.0 grams of a chloro-terminated methylphenylpolysilane (Mn=7,500 Mw/Mn=1.57). To the solution, 0.2 grams of triethylamine was added, 3 grams of water was added dropwise, and the mixture was agitated under reflux for 4 hours. At the end of reaction, 100 grams of toluene was added to the reaction solution, which was washed with 100 grams of water three times. The organic layer was dried overnight over calcium chloride. After the desiccant was filtered off, the organic layer was concentrated, obtaining 3.5 grams of a white powder.

The results of analysis of this white powder are shown below which indicate that it is a both end hydroxy-terminated methylphenylpolysilane.
Yield: about 75%
Mn: 7,550 (calculated as polystyrene)
Mw/Mn: 1.64
IR analysis: peak at 3624 cm$^{-1}$ (Si—OH)
OH quantity: 0.0260 mol/100 g (calculated: 0.0265 mol/100 g)

EXAMPLE 2

In 300 grams of THF was dissolved 15.0 grams of a chloro-terminated methylphenylpolysilane (Mn=5,600, Mw/Mn=1.66). To the solution, 1.2 grams of triethylamine was added, 10 grams of water was added dropwise, and the mixture was agitated under reflux for 4 hours. At the end of reaction, 300 grams of toluene was added to the reaction solution, which was washed with 300 grams of water three times. The organic layer was dried overnight over calcium chloride. After the desiccant was filtered off, the organic layer was concentrated, obtaining 11.3 grams of a white powder.

The results of analysis of this white powder are shown below which indicate that it is a hydroxy-terminated methylphenylpolysilane.
Yield: about 75%
Mn: 5,620 (calculated as polystyrene)
Mw/Mn: 2.09
IR analysis: peak at 3624 cm$^{-1}$ (Si—OH)
OH quantity: 0.0350 mol/100 g (calculated: 0.0356 mol/100 g)

Next, synthesis of dialkylhydroxy-terminated polysilanes and dialkylvinylsiloxy-terminated polysilanes from hydroxy-terminated polysilanes is described.

REFERENCE EXAMPLE 6

In 120 grams of toluene was dissolved 8.0 grams of hydroxy-terminated methylphenylpolysilane (Mn=5,620, Mw/Mn=2.09). To the solution, 1.0 grams of triethylamine was added, and 0.93 grams of dimethylhydrochlorosilane was added dropwise. Agitation was continued for 4 hours at room temperature. At the end of reaction, the reaction solution was washed with 100 grams of water three times. The organic layer was dried overnight over calcium chloride. After the desiccant was filtered off, the organic layer was concentrated, obtaining 6.6 grams of a white powder.

The results of analysis of this white powder are shown below which indicate that it is a dimethylhydrosiloxy-terminated methylphenylpolysilane.
Yield: about 80%
Mn: 5,900 (calculated as polystyrene)
Mw/mn: 2.19
IR analysis: peak at 3624 cm$^{-1}$ (Si—OH) disappeared peak at 2124 cm$^{-1}$ (Si—H)
Proton NMR: −0.8−0.6 ppm (SiCH$_3$)broad (in C$_6$D$_6$) 4.7-4.8 ppm (SiH) broad 6.2-7.6 ppm (Ph) broad

REFERENCE EXAMPLE 7

In 15 grams of toluene was dissolved 1.7 grams of hydroxy-terminated methylphenylpolysilane (Mn=7,550, Mw/Mn=1.64). To the solution, 1.4 grams of triethylamine was added, and 1.7 grams of dimethylvinylchlorosilane was added dropwise. Agitation was continued for 4 hours at 60° to 65° C. At the end of reaction, the reaction solution was washed with 50 grams of water three times. The organic layer was dried overnight over calcium chloride. After the desiccant was filtered off, the organic layer was concentrated, obtaining 1.4 grams of a white powder.

The results of analysis of this white powder are shown below which indicate that it is a dimethylvinylsiloxy-terminated methylphenylpolysilane.
Yield: about 80%
Mn: 7,900 (calculated as polystyrene)
Mw/Mn: 1.86
IR analysis: peak at 3624 cm$^{-1}$ (Si—OH) disappeared
Proton NMR: −0.8−0.6 ppm (SiCH$_3$)broad (in C$_6$D$_6$) 5.4−6.1 ppm (—CH=CH$_2$)broad 6.2-7.8 ppm (Ph) broad The process of the present invention facilitates synthesis of hydroxy-terminated polysilanes having a relatively high degree of polymerization. The hydroxy-terminated polysilanes allow various functional groups to be introduced therein and are useful source materials for forming copolymers with other polymers.

Although some preferred embodiments have been described, many modifications and variations may be made thereto in the light of the above teachings. It is therefore to be understood that within the scope of the appended claims, the invention may be practiced otherwise than as specifically described.

We claim:

1. A hydroxy-terminated polysilane of the formula:

$$OH[(R^1R^2Si)_n(R^3R^4Si)_m]_kOH$$

wherein R$^1$, R$^2$, R$^3$ and R$^4$ are independently monovalent hydrocarbon groups having 1 to 12 carbon atoms selected from substituted or unsubstituted alkyl and aryl groups, letters n, m and k are numbers in the range: $0 \leq n \leq 10$, $0 \leq m \leq 10$, $n+m \geq 10$, and $k \geq 1$.

2. A process for preparing a hydroxy-terminated polysilane of the formula:

$$OH[(R^1R^2Si)_n(R^3R^4Si)_m]_kOH$$

wherein R$^1$, R$^2$, R$^3$ and R$^4$ are independently monovalent hydrocarbon groups having 1 to 12 carbon atoms selected from substituted or unsubstituted alkyl and aryl groups, letters n, m and k are numbers in the range: $0 \leq n \leq 10$, $0 \leq m \leq 10$, $n+m \geq 10$, and $k \geq 1$, comprising hydrolyzing a chloro-terminated polysilane of the formula:

$$Cl[(R^1R^2Si)_n(R^3R^4Si)_m]_kCl$$

wherein R$^1$, R$^2$, R$^3$, R$^4$, n, m and k are defined above, in the presence of an amine in an amount of 2 mol or more per mol of said chloro-terminated polysilane and water in an amount of 2 mol or more per ml of said chloro-terminated polysilane.

3. The hydroxy-terminated polysilane according to claim 1, wherein $k \geq 5$.

4. The hydroxy-terminated polysilane according to claim 1, wherein $k \geq 10$.

5. The process for preparing a hydroxy-terminated polysilane according to claim 2, wherein said chloro-terminated polysilane of the formula:

$$Cl[(R^1R^2Si)_n(R^3R^4Si)_m]_kCl$$

is prepared by reacting at least one dichlorosilane with an alkali metal to form a polysilane of the formula:

$$(R^1R^2Si)_{n'}(R^3R^4Si)_{m'}$$

wherein $0 \leq n'$, $0 \leq m'$, $10 \leq n'+m'$; dissolving said polysilane in a chlorinated hydrocarbon solvent; exposing said polysilane dissolved in a chlorinated hydrocarbon solvent to UV radiation in an inert atmosphere to form said chloro-terminated polysilane, and adding hexane to precipitate said chloro-terminated polysilane.

6. The process for preparing a hydroxy-terminated polysilane according to claim 5, wherein said at least one dichlorosilane is selected from the group consisting of methylphenyldichlorosilane, ethylphenyldichlorosilane, methylethyldichlorosilane, methylpropyldichlorosilane, methylhexyldichlorosilane and dihexyldichlorosilane.

7. The process for preparing a hydroxy-terminated polysilane according to claim 5, wherein $30 \leq n'+m'$.

8. The process for preparing a hydroxy-terminated polysilane according to claim 5, wherein said polysilane has a number average molecular weight of 1,000 to 1,000,000.

9. The process for preparing a hydroxy-terminated polysilane according to claim 5, wherein said polysilane has a number average molecular weight of 5,000 to 1,000,000.

10. The process for preparing a hydroxy-terminated polysilane according to claim 5, wherein said chlorinated hydrocarbon solvent is selected from the group consisting of dichloromethane, chloroform, carbon tetrachloride, 1,2-dichloroethane, 1,1,2-trichloroethane and 1,1,2,2-tetrachloroethane.

11. The process for preparing a hydroxy-terminated polysilane according to claim 5, wherein said polysilane is dissolved in said chlorinated hydrocarbon solvent at a concentration of 1 to 20% by weight.

12. The process for preparing a hydroxy-terminated polysilane according to claim 5, wherein said polysilane is dissolved in said chlorinated hydrocarbon solvent at a concentration of 1 to 10% by weight.

13. The process for preparing a hydroxy-terminated polysilane according to claim 2, wherein said chloro-terminated polysilane is first dissolved in a polysilane-miscible solvent selected from tetrahydrofuran, toluene and xylene, before hydrolysis.

14. The process for preparing a hydroxy-terminated polysilane according to claim 2, wherein said chloro-terminated polysilane is selected from the group consisting of chloro-terminated methylhexylpolysilane and chloro-terminated methyphenylpolysilane.

15. The process for preparing a hydroxy-terminated polysilane according to claim 2, wherein said amine is selected from the group consisting of triethylamine and pyridine.

* * * * *